US008652832B2

(12) United States Patent
Kondo

(10) Patent No.: US 8,652,832 B2
(45) Date of Patent: Feb. 18, 2014

(54) AUTOMATED ANALYZER

(75) Inventor: Yasushi Kondo, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 13/329,403

(22) Filed: Dec. 19, 2011

(65) Prior Publication Data
US 2012/0156764 A1    Jun. 21, 2012

(30) Foreign Application Priority Data

Dec. 20, 2010    (JP) ................................. 2010-283386

(51) Int. Cl.
C12M 1/34 (2006.01)
C12M 3/00 (2006.01)
G01N 33/48 (2006.01)
G01N 33/50 (2006.01)
G01N 1/10 (2006.01)
G01J 3/30 (2006.01)

(52) U.S. Cl.
USPC ................. 435/287.1; 435/287.3; 435/288.1; 356/246; 356/315; 702/19

(58) Field of Classification Search
USPC ........ 435/283.1–309.4; 356/246, 315; 702/19
See application file for complete search history.

(56) References Cited

U.S. PATENT DOCUMENTS 4,312,591 A * 1/1982 Tomoff .......................... 356/315
2011/0093207 A1 * 4/2011 Ingber et al. ..................... 702/19

FOREIGN PATENT DOCUMENTS

JP     1062435 A     3/1998
JP     2010217057 A    9/2010

* cited by examiner

Primary Examiner — Nathan Bowers
Assistant Examiner — Lydia Edwards
(74) Attorney, Agent, or Firm — The Webb Law Firm

(57) ABSTRACT

The automatic analyzer repeatedly performs a first processing operation for creating a pretreated specimen with a pretreatment solution in a first reaction cell. The analyzer also repeatedly performs a second processing operation for creating a reacted specimen by reacting the pretreated specimen with a reagent in a second reaction cell. In a first control operation, a turntable is rotated through a first angle in a first direction and halted. In a second control operation, the turntable is rotated through a second angle in a second direction and halted. The second reaction cell is spaced by a second angle in a first direction from the first reaction cell. The turntable is so rotated that the first and second reaction cells are halted at least in first, second, and third positions.

9 Claims, 9 Drawing Sheets

AUTOMATED ANALYZER

BACKGROUND OF THE INVENTION

1. Field of the Invention

The present invention relates to an automated analyzer.

2. Description of Related Art

Automated analyzers are known which accept biological samples (such as serum, blood cells, urine, and cerebrospinal fluid) as specimens, cause the specimens to react with reagents, and perform analysis of various components such as sugars, cholesterols, proteins, and enzymes.

In such an automated analyzer, specimens may need to be pretreated depending on measurement items. For example, before a specimen is reacted with a reagent, the specimen is diluted or a pretreatment solution is added to the specimen.

For example, JP-A-H10-62435 discloses an automated biochemical analyzer which injects aliquots of biological samples from sample containers set on a sample turntable into dilution containers set on a dilution turntable by means of sample-diluting pipettes (probes), injects a diluting fluid into the dilution containers to dilute the aliquots of biological sample to a given proportion, dispenses aliquots of the diluted biological samples from the dilution containers into reaction containers set on a reaction turntable by means of sampling pipettes, add dispense reagents from reagent disks, adds the reagents to the reaction containers by reagent pipettes, and analyzes the biological samples in terms of plural items.

The automated analyzer described in this patent document has the dilution turntable on which the dilution containers for diluting samples are set and the reaction turntable on which the reaction containers for reacting diluted biological samples with reagents are set. That is, dilution (pretreatment) of samples and reactions of the diluted biological samples with the reagents are performed on the different turntables.

In an automated analyzer in which pretreatment of samples and reactions of the samples with reagents are performed on different turntables, the instrument tends to be large in size and complicated.

In view of this problem, an automated analyzer has been developed in which pretreatment of samples and reactions of the samples with reagents are conducted on the same turntable. For example, JP-A-2010-217057 discloses an automated analyzer having a sample aliquot dispensing mechanism including aliquot dispensing arms, a horizontal arm, and a vertical rail. Reactions of specimens with reagents and pretreatment of the specimens using pretreatment solutions are carried out on a common disk. The dispensing mechanism has free access to a container in any position on the turntable and injects an aliquot of sample and an aliquot of pretreated sample.

The automated analyzer described in this patent document, however, needs to be equipped with a mechanism for moving the aliquot dispensing mechanism over the common disk. This may complicate the instrument.

In recent years, there has been a demand for an automated analyzer which is neither large in size nor complicated but provides improved processing capabilities. However, as described previously, in the automated analyzers described in the above noted patent documents, the instruments may be large in size or complicated.

SUMMARY OF THE INVENTION

In view of the foregoing problems, the present invention has been made. Some embodiments of the invention provide automated analyzers capable of providing improved processing capabilities without increasing the size of the instrument or complicating it.

(1) An automated analyzer associated with the present invention for performing a first processing operation to create a pretreated specimen by pretreating a specimen with a pretreatment solution in first reaction cells and a second processing operation to create a reacted specimen by reacting the pretreated specimen with a reagent in second reaction cells. The analyzer includes a turntable on which the first and second reaction cells are arranged annularly, control means for controlling rotation of the turntable, first aliquot dispensing means for selectively pour out the pretreatment solution and the reagent in a first position, second aliquot dispensing means for selectively performing dispensing of aliquots of the specimen and injection of aliquots of the pretreated specimen in a second position, stirring means for selectively performing stirring of the pretreatment solution and the specimen and stirring of the pretreated specimen and the reagent in a third position, and measuring means for measuring the reacted specimen. The control means repeatedly performs a first control operation for rotating the turntable through a first angle in a first direction and then bringing the turntable to a halt and a second control operation for rotating the turntable through a second angle in a second direction opposite to the first direction and then bringing the turntable to a halt. The second reaction cells are spaced by the second angle in the first direction from the first reaction cells. The turntable is so rotated that the first and second reaction cells are halted at least in the first, second, and third positions by repetitive execution of the first control operation and the second control operation. The second aliquot dispensing means sucks the pretreated specimen when the first reaction cell containing the pretreated specimen is halted in the second position and pours out the sucked pretreated specimen when the second reaction cell is halted in the second position.

In this automated analyzer, the controller performs the first control operation for bringing the turntable to a halt after it is rotated through the first angle in the first direction and the second control operation for bringing the turntable to a halt after it is rotated through the second angle in the second direction. Therefore, while the turntable is making its first rotation, the first reaction cells are brought to a halt in the first, second, and third positions and the first processing operation can be carried out. Then, while the turntable is making its second rotation, the first reaction cells are brought to a halt again in the first, second, and third positions, and the second reaction cells are halted in the first, second, and third positions. The second processing operation can be carried out. Consequently, the first and second processing operations can be performed on the same turntable. In addition, the first aliquot dispensing means, the second aliquot dispensing means, and the stirring means can perform their processing operations efficiently in their respective one positions. Accordingly, the processing capabilities can be enhanced without increasing the size of the instrument or complicating it.

According to this automated analyzer, the first aliquot dispensing means, the second aliquot dispensing means, and the stirring means can be operated efficiently as described later. Hence, the processing capabilities can be improved.

(2) In one aspect of the automated analyzer associated with the invention, the angle made between the first and second positions and the angle made between the second and third positions may be equal to the difference between the first and second angles, and the angle made between the third and first positions may be equal to the first angle.

(3) In another aspect of the automated analyzer associated with the invention, owing to the first and second control operations, the turntable moves the first reaction cell located in the first position into a fourth position spaced by the second angle in the first direction from the second position, halts the cell, and then halts it. Subsequently, the turntable moves the cell from the fourth position to the second position and halts the cell. The turntable then moves the first reaction cell located in the second position into a fifth position spaced by the second angle in the first direction from the second position and halts the cell. Then, the turntable moves the cell from the fifth position into the third position and halts the cell. Thereafter, the turntable moves the first reaction cell located in the third position into the first position and halts the cell. The turntable then moves the cell into a sixth position spaced by the second angle in the second direction from the first position and halts the cell. The turntable then moves the first reaction cell located in the sixth position into the second position and halts the cell. The turntable then moves the cell into a seventh position spaced by the second angle in the second direction from the second position and brings the cell to a halt.

(4) In a further aspect of the automated analyzer associated with the invention, the second angle may be smaller than the first angle.

In this automated analyzer, the time taken for the turntable to make one rotation can be shortened.

(5) In a yet other aspect of the automated analyzer associated with the invention, the second aliquot dispensing means may inject aliquots of the pretreated specimen into the second reaction cells in which the aliquots of the reagent have been injected.

According to this automated analyzer, the second aliquot dispensing means can easily pour out the pretreated specimen into the second reaction cells, because there is the reagent in the second reaction cells.

BRIEF DESCRIPTION OF THE TABLES

Figure 1:
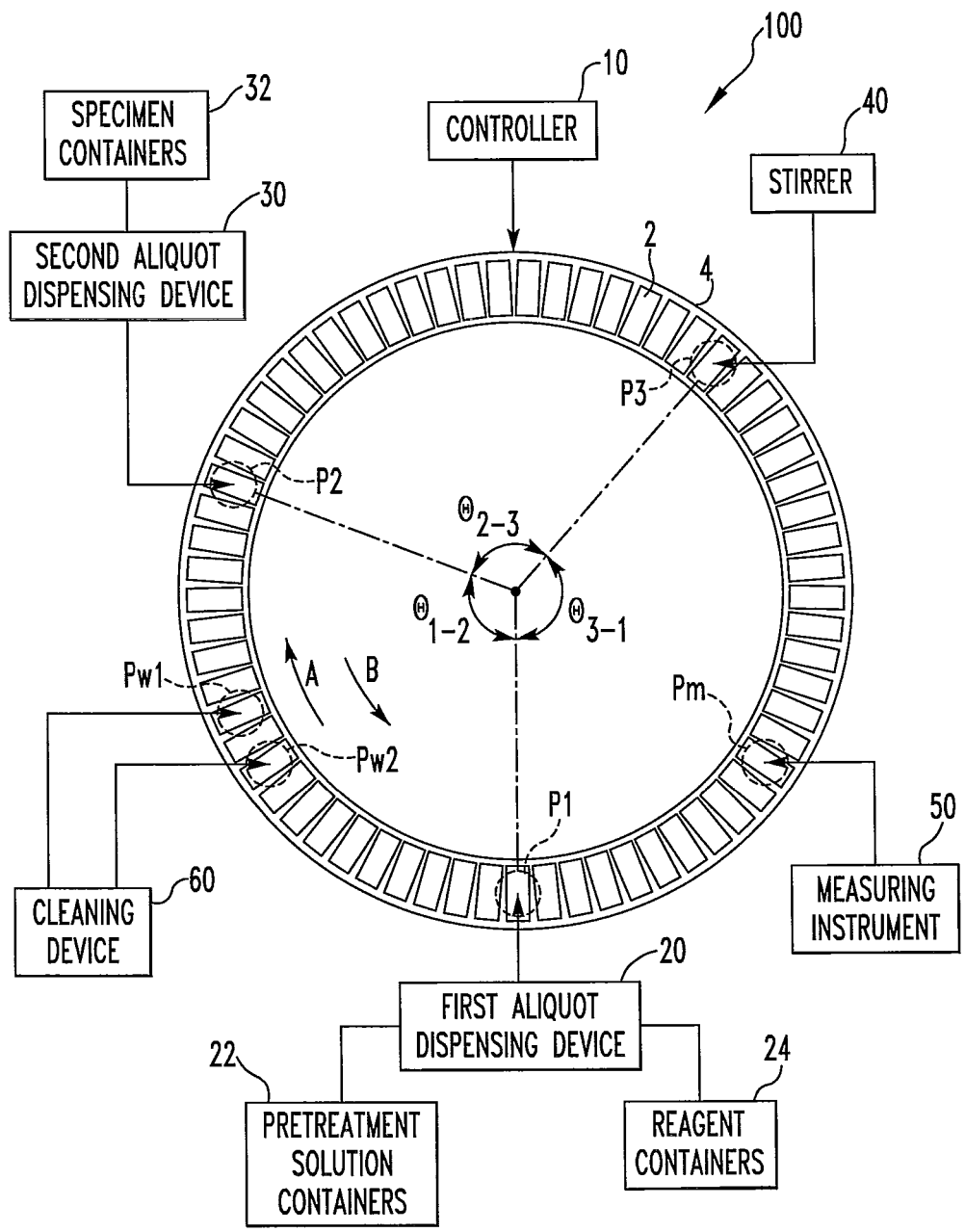
FIG. 1 is a schematic diagram of an automated analyzer associated with an embodiment of the present invention.

Table I is a table illustrating the flow of operation of the first aliquot dispensing device of the automated analyzer shown in FIG. 1;

Table II is a table illustrating the flow of operation of the second aliquot dispensing device of the automated analyzer shown in FIG. 1; and Table III is a table illustrating the flow of operation of the stirrer of the automated analyzer shown in FIG. 1.

DESCRIPTION OF THE PREFERRED EMBODIMENTS

The preferred embodiments of the present invention are hereinafter described in detail with reference to the drawings. It is to be noted that the embodiments described below do not unduly restrict the contents of the present invention set forth in the appended claims. Furthermore, all of the configurations described below are not always the essential components of the invention.

1. Automated Analyzer

First, the configuration of an automated analyzer associated with an embodiment of the present invention is described. FIG. 1 is a schematic diagram illustrating the automated analyzer associated with the present embodiment. The analyzer, generally indicated by reference numeral 100, can perform a first processing operation for pretreating a specimen with a pretreatment solution and a second processing operation for injecting aliquots of the pretreated specimen into other reaction cells to cause the specimen to react with reagents. The pretreatment of the specimen includes dilution of the specimen.

Referring still to FIG. 1, the automated analyzer 100 can include a turntable 4 on which plural reaction cells 2 are arranged, a controller 10, a first aliquot dispensing device 20, a second aliquot dispensing device 30, a stirrer 40, a measuring instrument 50, and a cleaning device 60.

Each of the reaction cells 2 is a container accommodating a specimen. Within the cell 2, a pretreatment of the specimen and a reaction of the specimen with a reagent can be performed. For example, the specimen is a biological specimen such as serum, blood cells, urine, or cerebrospinal fluid. The reaction cells 2 are arranged annularly on the turntable 4. For instance, the cells 2 are arranged along the outer periphery of the circular turntable 4. No restriction is imposed on the number of the arranged reaction cells 2. The number can be increased and reduced according to the need. The cells 2 are arranged, for example, at regular intervals. As the turntable 4 rotates, the position of each cell 2 moves.

The turntable 4 has a central rotatable shaft (not shown) about which the body of the turntable 4 can rotate. The rotation of the turntable 4 is controlled by the controller 10. Disposed around the turntable 4 are the controller 10, the devices 20, 30, the stirrer 40, the instrument 50, the device 60, and containers 22, 24, 32. In the automated analyzer 100, the first and second processing operations can be performed on the single turntable 4.

The controller 10 that is one example of control means can control the rotation of the turntable 4. The controller 10 repeatedly performs a first control operation for rotating the turntable 4 through a first angle in a first direction A and then halting the turntable and a second control operation for rotating the turntable 4 through a second angle in a second direction B opposite to the first direction A and then halting the turntable. Thus, the controller 10 repeatedly rotates and halts the turntable 4 to bring each reaction cell 2 to a halt at first, second, and third positions P1, P2, and P3 in turn.

The time for which each reaction cell 2 is halted by the first control operation may be hereinafter referred to as the first period of time. The time for which each reaction cell 2 is halted by the second control operation may be hereinafter referred to as the second period of time. As long as the devices 20, 30, 40, 50, and 60 can perform processing operations described later, no restrictions are placed on the first and second periods of time but rather the first and second periods can be set at will. For example, the second period can be set longer than the first period.

For example, the controller 10 performs the first control operation to rotate the turntable 4 through 120° in the first direction A and to halt the turntable for 0.3 to 0.6 second. The controller then performs the second control operation to rotate the turntable 4 through 3° in the second direction B and then to halt the turntable for 0.3 to 0.6 second. The single first operation and the single second control operation constitute one cycle of operation. The controller 10 repeats the cycle of operation. During one cycle of operation, the turntable 4 rotates through 117° (120°–3°) in the first direction A. Consequently, the reaction cell 2 located in the first position P1 can be moved into the second position P2. The reaction cell 2 located in the second position P2 can be moved into the third position P3. As this cycle of operation is repeated, the turntable 4 can bring each reaction cell 2 to a halt in the positions P1 to P3 in turn. Further details will be described later in connection with the operation of the automated analyzer.

During the first and second control operations, the turntable 4 rotates. In the illustrated example, the first direction A is a clockwise direction. The second direction B is a counterclockwise direction. However, no restrictions are placed on these directions, as long as the direction of rotation is reversed between the first and second control operations.

The first aliquot dispensing device 20 that is one example of first aliquot dispensing means pours out a pretreatment solution and a reagent selectively in the first position P1. The first aliquot dispensing device 20 injects aliquots of the pretreatment solution in the first processing operation and injects aliquots of the reagent in the second processing operation. In particular, the first aliquot dispensing device 20 can inject aliquots of the pretreatment solution by sucking the pretreatment solution from the pretreatment solution container 22 and pouring out the sucked pretreatment solution into the reaction cell 2 halted in the first position P1. The pretreatment solution may be a diluting fluid for diluting a specimen. Furthermore, the first aliquot dispensing device 20 can divide a reagent into aliquots and inject them by sucking the reagent from the reagent container 24 and pouring out the sucked reagent into the reaction cell 2 halted in the first position P1.

For example, the first aliquot dispensing device 20 has a pipette (probe) for sucking and pouring out a pretreatment solution and a reagent and a moving mechanism for moving the pipette between the first position P1 and the pretreatment solution container 22 and between the first position P1 and the reagent container 24. The first aliquot dispensing device 20 may have a plurality of pipettes.

For example, the automated analyzer 100 may have a plurality of pretreatment solution containers 22. The first aliquot dispensing device 20 may extract a specified container 22 from the pretreatment solution containers 22 and suck a pretreatment solution from the extracted container. Furthermore, the automated analyzer 100 may have a plurality of reagent containers 24, and the first aliquot dispensing device 20 may extract a specified container 24 from the reagent containers 24 and suck a reagent from the extracted container.

The second aliquot dispensing device 30 that is one example of second aliquot dispensing means selectively performs delivery of the specimen and injection of an aliquot of the pretreated specimen in the second position P2. The second aliquot dispensing device 30 injects an aliquot of the specimen into the reaction cell 2 halted in the second position P2 during the first processing operation and injects an aliquot of the pretreated specimen during the second processing operation. Specifically, the second aliquot dispensing device 30 can inject an aliquot of a specimen by sucking the specimen from the specimen container 32 and pouring out the sucked specimen into the reaction cell 2 halted in the second position P2. The specimen containers 32 may be plural in number and arranged on a turntable (not shown). The second aliquot dispensing device 30 may extract a specified specimen container 32 from the specimen containers 32 on the turntable and suck a specimen from the extracted container. Furthermore, the second aliquot dispensing device 30 can inject an aliquot of a pretreated specimen by sucking the pretreated specimen from within the first reaction cell 2 halted in the second position P2 and pouring out the sucked pretreated specimen into other second reaction cell 2 halted in the second position P2.

For example, the second aliquot dispensing device 30 has a pipette (probe) for sucking a specimen and pouring out the specimen that has been pretreated and a moving mechanism for moving the pipette between the second position P2 and the specimen container 32. The second aliquot dispensing device 30 may have a plurality of pipettes.

The stirrer 40 that is one example of stirring means selectively performs stirring of a pretreatment solution and a specimen and stirring of a pretreated specimen and a reagent in the third position P3. During the first processing operation, the stirrer 40 stirs the specimen and pretreatment solution in the reaction cell 2 halted in the third position P3. During the second processing operation, the stirrer 40 stirs the pretreated specimen and reagent. For example, the stirrer 40 has a stirring probe (stirring rod) for stirring the specimen and pretreatment solution and stirring the pretreated specimen and reagent and a rod-driving mechanism for rotating or reciprocating the stirring rod. Additionally, the stirrer 40 may have a cleaning mechanism for cleaning the stirring probe.

The measuring instrument 50 that is one example of measuring means measures various components (such as sugars, cholesterols, proteins, and enzymes) of a specimen that has been reacted with the reagent within the reaction cell 2 passing across a measurement position Pm. The measurement position Pm can be set at an arbitrary position. For example, the measuring instrument 50 has a spectrometer which, when light is directed at a measured object or specimen, electrically detects the amount of light transmitted through the specimen. Data obtained by the measurement is converted into digital numerical values by an analog-to-digital converter, arithmetically processed by a CPU, and the results are output.

For example, the cleaning device 60 has a waste liquid pump and a cleaning liquid pump (none of which are shown). The cleaning device 60 sucks the already measured reaction specimen within the reaction cell 2 halted in a first cleaning position Pw1 and the pretreated specimen no longer required by means of the waste liquid pump and discharges them into a waste liquid tank. When this reaction cell 2 halts in a second cleaning position Pw2, the cleaning device 60 supplies a cleaning liquid into the reaction cell 2 by the cleaning liquid pump, cleans the interior of the reaction cell 2 by the cleaning liquid, and then discharges the cleaning liquid into the waste liquid tank. The first and second cleaning positions Pw1 and Pw2 can be set at will.

In the automated analyzer 100, the angle $\theta_{1-2}$ made between the first position P1 and the second position P2 around the axis of rotation of the turntable 4 is equal to the difference between the first and second angles. Similarly, the angle $\theta_{2-3}$ made between the second position P2 and the third position P3 is equal to the difference between the first and second angles. The angle $\theta_{3-1}$ made between the third position P3 and the first position P1 is equal to the first angle. The second reaction cell 2 in which the second processing operation is performed is spaced by the second angle in the first direction A from the first reaction cell 2 in which the first processing operation is performed. Consequently, while the turntable 4 is making its first rotation, the first reaction cell 2 can be halted in the first position P1, second position P2, and third position P3 in turn and the first processing operation can be performed. While the turntable 4 is then making its second rotation, the first reaction cell 2 can be halted again in the first position P1, second position P2, and third position P3, and the second reaction cell 2 can be halted in the first position P1, second position P2, and third position P3. The second processing operation can be performed. Therefore, the second aliquot dispensing device 30 can suck the pretreated specimen when the first reaction cell 2 containing the pretreated specimen is halted in the second position P2 and pour out the pretreated specimen when the second reaction cell 2 is halted in the second position P2. Details will be described later in connection with the operation of the automated analyzer.

No restrictions are imposed on the magnitudes of the first and second angles as long as the aforementioned relationship is satisfied. However, the second angle is preferably smaller than the first angle, in which case the time taken for the turntable 4 to turn once can be shortened.

2. Operation of the Automated Analyzer

The operation of the automated analyzer associated with the present embodiment is next described.

In the automated analyzer 100, the first processing operation is performed in a first reaction cell on the turntable 4 for one specimen. The second processing operation is performed in a second reaction cell spaced by the second angle in the first direction A from the first reaction cell. In particular, an aliquot of a pretreatment solution is first injected into the first reaction cell 2 by the first aliquot dispensing device 20. An aliquot of a specimen is injected by the second aliquot dispensing device 30 into the first reaction cell 2 already holding the pretreatment solution. The pretreatment solution and specimen are stirred by the stirrer 40 to create a pretreated specimen, and the first processing operation is effected. Then, an aliquot of a reagent is injected into the second reaction cell 2 by the first aliquot dispensing device 20. An aliquot of the pretreated specimen held in the first reaction cell 2 is injected into the second reaction cell 2 by the second aliquot dispensing device 30. The reagent and the pretreatment solution are stirred by the stirrer 40 to create a reacted specimen. Thus, the second processing operation is carried out. The reacted specimen is measured by the measuring instrument 50. The automated analyzer 100 can perform the first and second processing operations in parallel for plural specimens. Further details are described below.

FIGS. 2-9 illustrate the operation of the automated analyzer 100. In FIGS. 2-9, the devices 10-60 are omitted from being shown for convenience. Furthermore, in FIGS. 2-9, only reaction cells 2 necessary for illustration of the operation of the automated analyzer 100 are shown; other reaction cells 2 are omitted from being shown.

Figure 2:
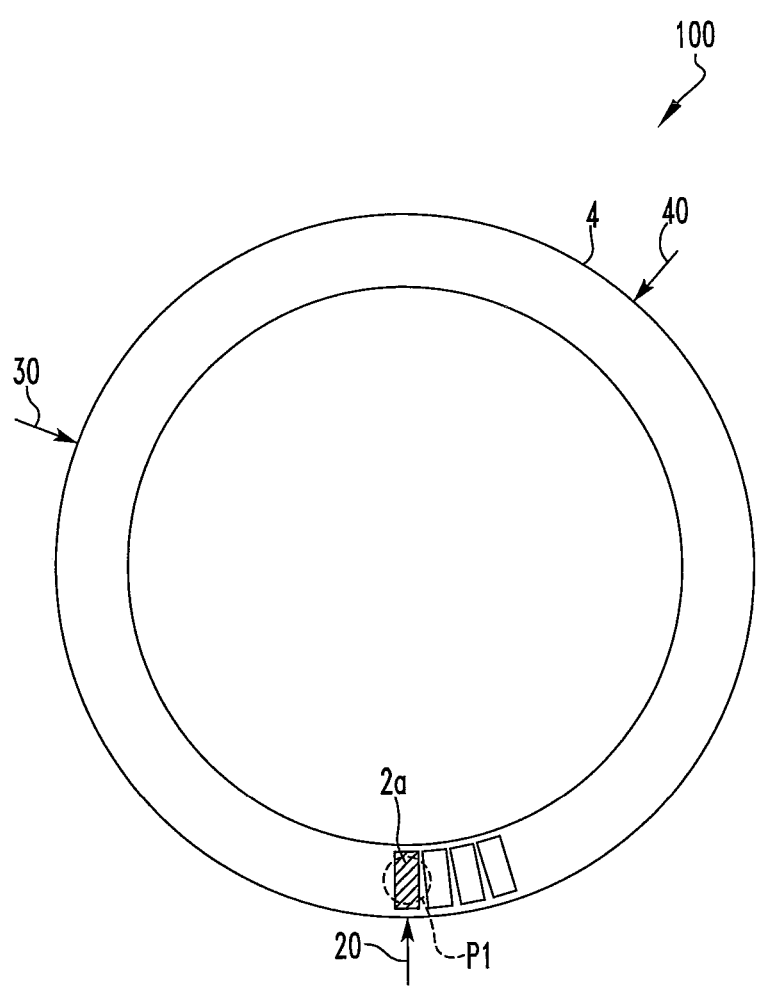
FIG. 2 is a plan view of the automated analyzer shown in FIG. 1, illustrating the operation.

As shown in FIG. 2, the first aliquot dispensing device 20 injects an aliquot of the pretreatment solution into the reaction cell 2a located in the first position P1. More specifically, the first aliquot dispensing device 20 draw in the pretreatment solution from the pretreatment solution container 22 (see FIG. 1) and pours out the sucked liquid into the reaction cell 2a located in the first position P1.

The controller 10 subsequently performs the first control operation to rotate the turntable 4 through the first angle in the first direction A and halt the turntable for the first period of time. Then, the controller 10 performs the second control operation to rotate the turntable 4 through the second angle in the second direction B and halt the turntable for the second period. Thus, one cycle of operation is performed. The automated analyzer 100 repeats the cycle to carry on the processing.

Figure 3A:
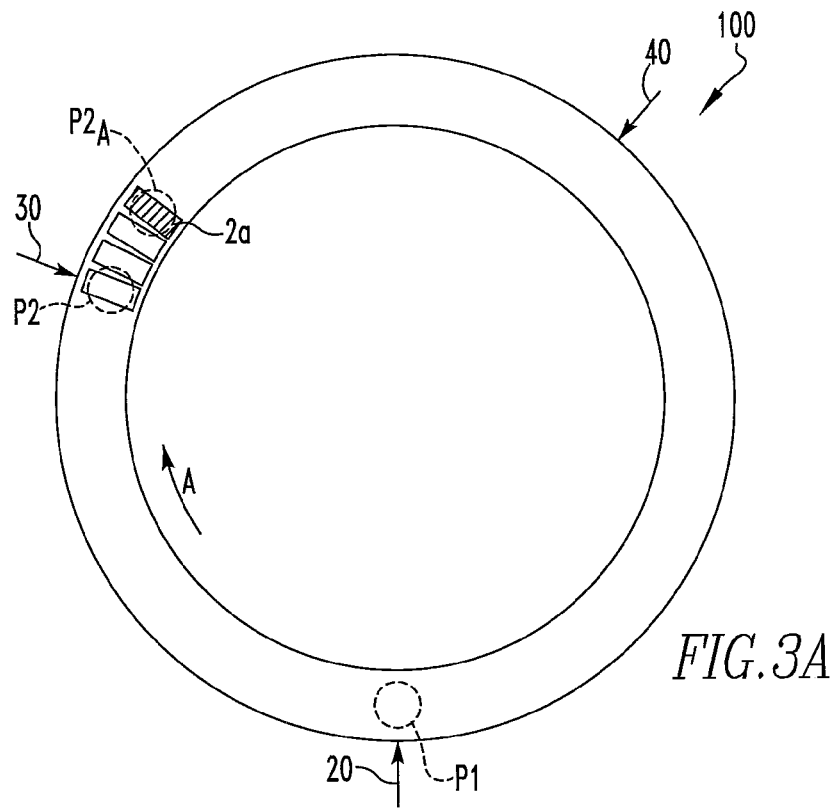
FIGS. 3A and 3B are plan views of the automated analyzer shown in FIG. 1, illustrating the operation.

As shown in FIG. 3A, the controller 10 performs a first cycle of the first control operation to cause the turntable 4 to move the reaction cell 2a located in the first position P1 into a fourth position $P2_A$ spaced by the second angle in the first direction A from the second position P2 and to halt the cell for the first period of time.

Figure 3B:
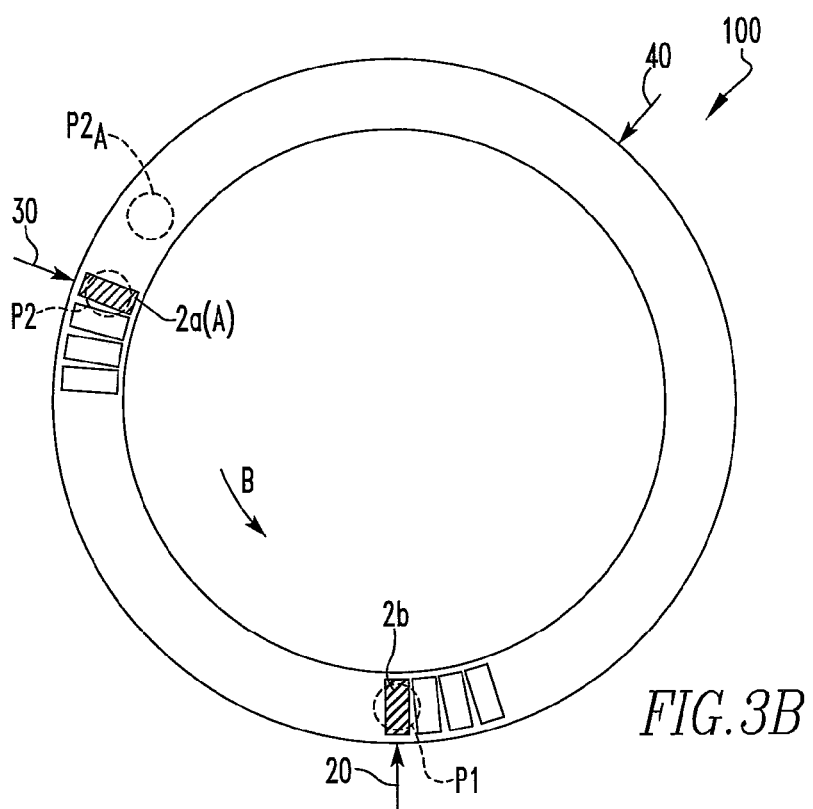

As shown in FIG. 3B, the controller 10 performs a first cycle of the second control operation to cause the turntable 4 to move the reaction cell 2a located in the fourth position $P2_A$ into the second position P2 and to halt the cell for the second period.

During the second period of time, the second aliquot dispensing device 30 pours out specimen A into the reaction cell 2a. In particular, the second aliquot dispensing device 30 previously sucks a specimen from the specimen container 32 and pours out the sucked specimen into the reaction cell 2a during the second period of time. In the second period, the first aliquot dispensing device 20 pours out the pretreatment liquid into the reaction cell 2b halted in the first position P1.

The second aliquot dispensing device 30 sucks specimen B from the specimen container 32 after the specimen is poured into the reaction cell 2a until the reaction cell 2b is halted in the second position P2. In this way, the second aliquot dispensing device 30 sucks a specimen from the specimen container 32 during the period starting with delivery of the specimen into the reaction cell 2 and ending with a halt of the next reaction cell 2 in the second position P2, the halt persisting for the second period.

Figure 4A:
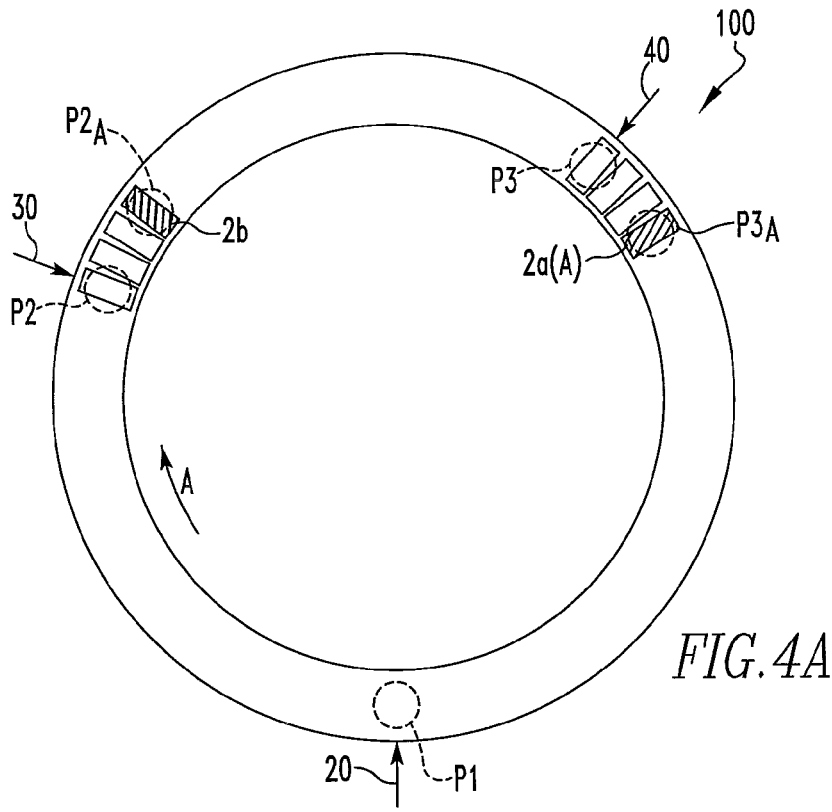
FIGS. 4A and 4B are plan views of the automated analyzer shown in FIG. 1, illustrating the operation.

As shown in FIG. 4A, the controller 10 performs a second cycle of the first control operation to cause the turntable 4 to move the reaction cell 2a located in the second position P2 into a fifth position $P3_A$ spaced by the second angle in the first direction A from the third position P3. The reaction cell 2b located in the first position P1 is moved into the fourth position $P2_A$ and halted for the first period of time.

Figure 4B:
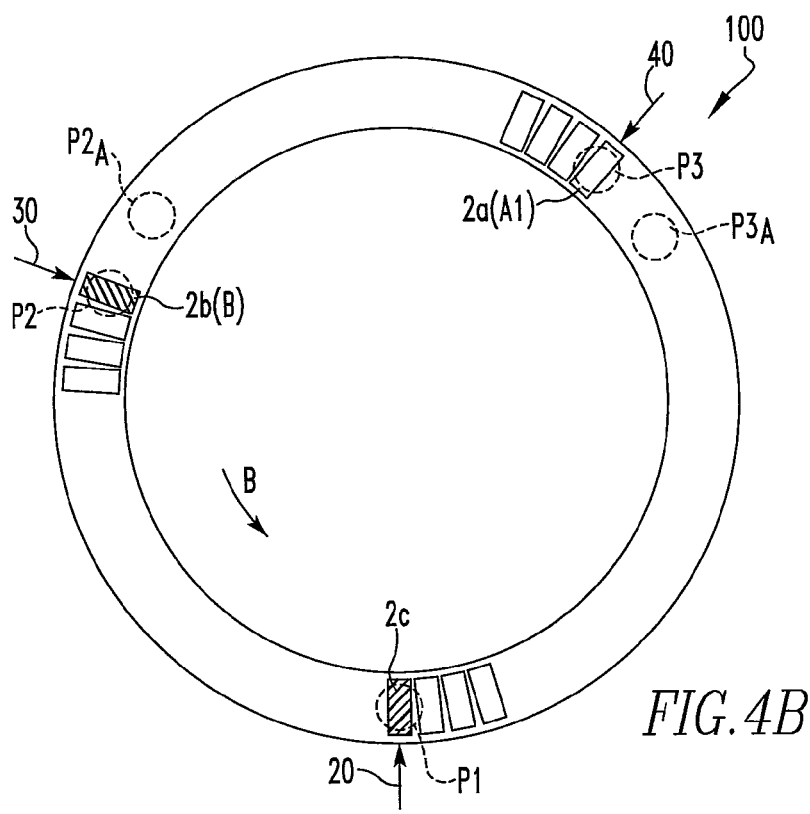

As shown in FIG. 4B, the controller 10 performs a second cycle of the second control operation to cause the turntable 4 to move the reaction cell 2a located in the fifth position $P3_A$ into the third position P3, to move the reaction cell 2b located in the fourth position $P2_A$ into the second position P2, and to halt the cell for the second period of time.

During the second period of time, the stirrer 40 stirs together the specimen A and pretreatment solution within the reaction cell 2a to thereby create a pretreated specimen A1 within the reaction cell 2a. Furthermore, during the second period, the second aliquot dispensing device 30 pours out the specimen B into the reaction cell 2b. In addition, during the second period, the first aliquot dispensing device 20 pours out the pretreatment solution into the reaction cell 2c halted in the first position P1.

The stirrer 40 cleans the stirring probe used for stirring of the specimen and pretreatment solution within the reaction cell 2a until the next reaction cell 2b comes to a halt in the third position P3. In this way, the stirrer 40 cleans the stirring probe after stirring the interior of the reaction cell 2 until the next reaction cell 2 comes to a halt in the third position P3.

After pouring out the pretreatment solution into the reaction cell 2c, the first aliquot dispensing device 20 sucks a reagent from the reagent container 22 (see FIG. 1) until the next reaction cell 2d comes to a halt in the first position P1. In this way, the first aliquot dispensing device 20 sucks a reagent or pretreatment solution after the pretreatment solution or reagent is delivered into the reaction cell 2 until the next reaction cell 2 halts in the first position P1.

Figure 5A:
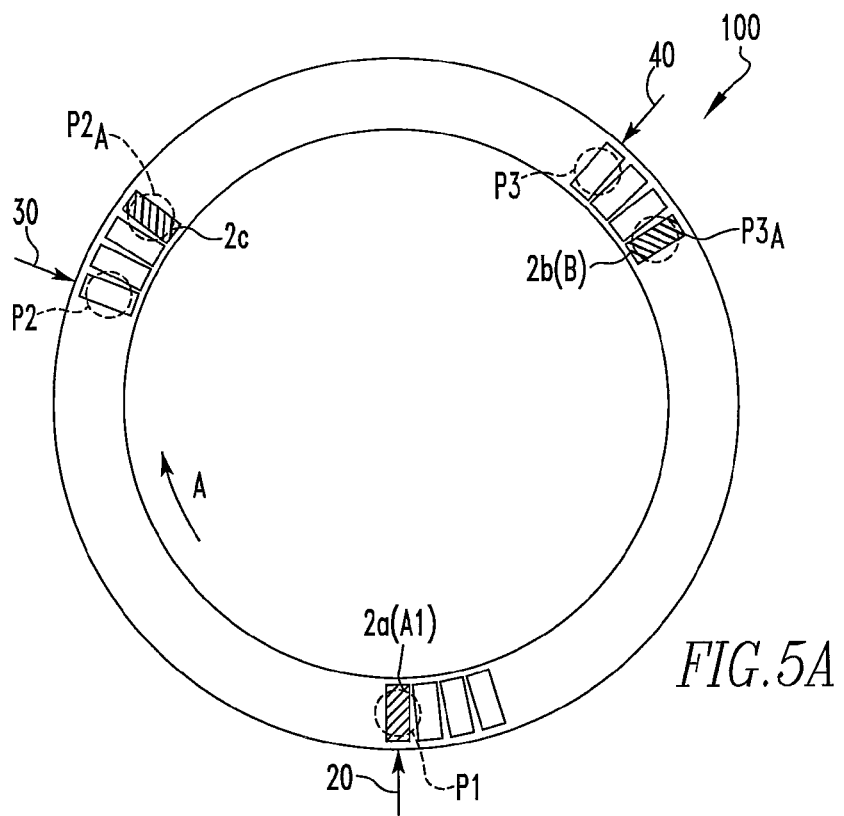
FIGS. 5A and 5B are plan views of the automated analyzer shown in FIG. 1, illustrating the operation.

As shown in FIG. 5A, the controller 10 performs a third cycle of the first control operation to cause the turntable 4 to move the reaction cell 2a located in the third position P3 into the first position P1, to move the reaction cell 2b located in the second position P2 into the fifth position P3$_A$, and to move the reaction cell 2c located in the first position P1 into the fourth position P2$_A$. The cells are halted for the first period.

Figure 5B:
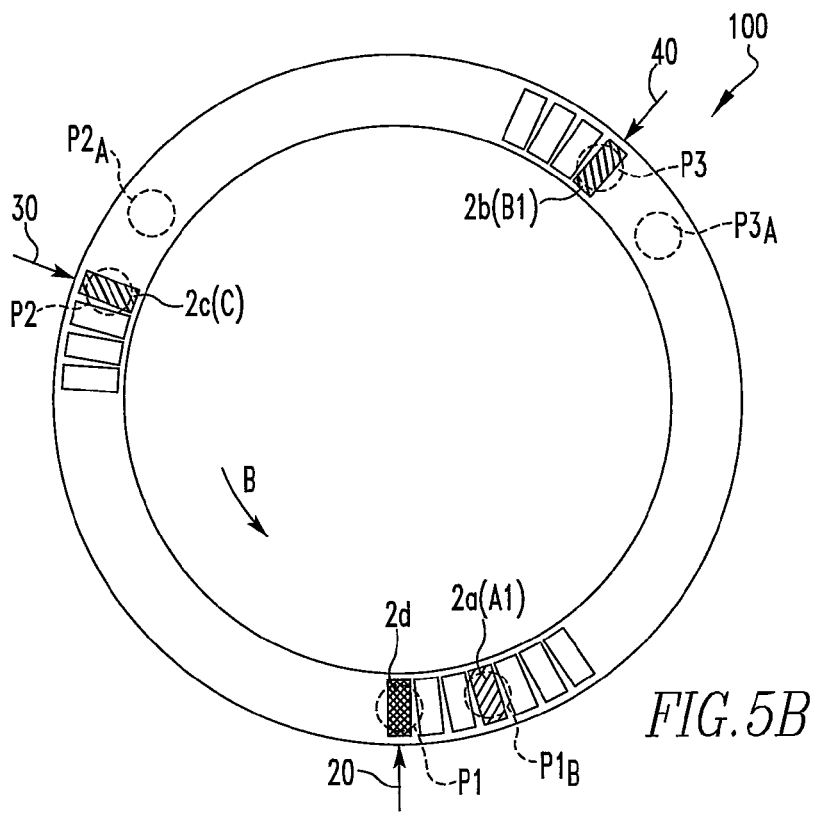

As shown in FIG. 5B, the controller 10 performs a third cycle of the second control operation to cause the turntable 4 to move the reaction cell 2a located in the first position P1 into a sixth position P1$_B$ spaced by the second angle in the second direction B from the first position P1, to move the reaction cell 2b located in the fifth position P3$_A$ into the third position P3, and to move the reaction cell 2c located in the fourth position P2$_A$ into the second position P2. The cells are halted for the second period of time.

During the second period, the first aliquot dispensing device 20 ejects a reagent into the reaction cell 2d halted in the first position P1. The cell 2d is spaced by the second angle (corresponding to two reaction cells in this embodiment) in the first direction A from the reaction cell 2a. Furthermore, during the second period, the second aliquot dispensing device 30 pours out a specimen C into the reaction cell 2c. In addition, during the second period, the stirrer 40 stirs together the specimen B and pretreatment solution in the reaction cell 2b. As a result, a pretreated specimen B1 is created in the reaction cell 2b.

Figure 6A:
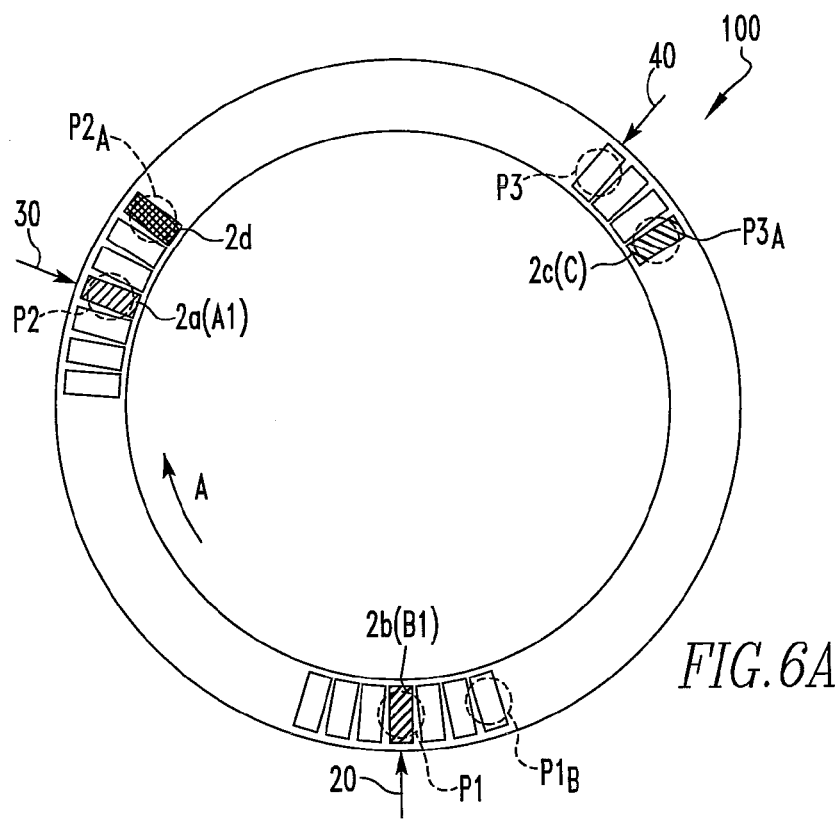
FIGS. 6A and 6B are plan views of the automated analyzer shown in FIG. 1, illustrating the operation.

As shown in FIG. 6A, the controller 10 performs a fourth cycle of the first control operation to cause the turntable 4 to move the reaction cell 2a located in the position P1$_B$ into the second position P2, to move the reaction cell 2d located in the first position P1 into the fourth position P2$_A$, to move the reaction cell 2b located in the third position P3 into the first position P1, and to move the reaction cell 2c located in the second position P2 into the position P3$_A$. The cells are halted for the first period of time.

During the first period, the second aliquot dispensing device 30 take in the pretreated specimen A1 from within the reaction cell 2a.

Figure 6B:
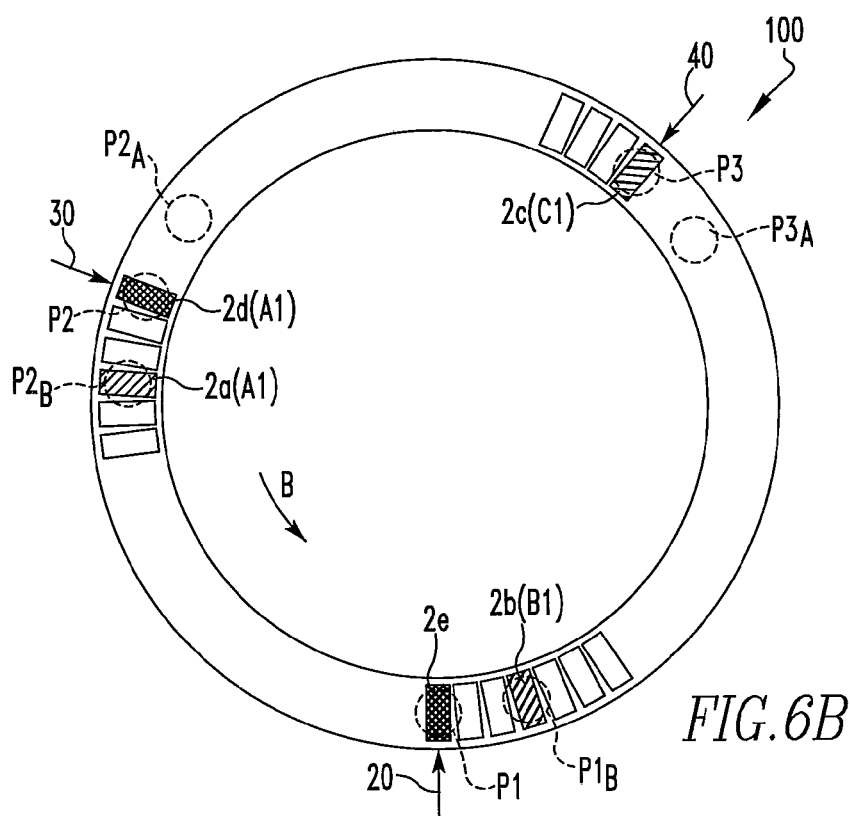

As shown in FIG. 6B, the controller 10 performs a fourth cycle of the second control operation to cause the turntable 4 to move the reaction cell 2a located in the second position P2 into a seventh position P2$_B$ located more forwardly in the second direction B than the second position P2, to move the reaction cell 2d located in the fourth position P2$_A$ into the second position P2, to move the reaction cell 2b located in the first position P1 into the position P1$_B$, and to move the reaction cell 2c located in the position P3$_A$ into the third position P3. The cells are halted for the second period of time.

During the second period, the first aliquot dispensing device 20 pours out a reagent into a reaction cell 2e halted in the first position P1. For example, the cell 2e is spaced by the second angle from the reaction cell 2b in the first direction A. Furthermore, during the second period, the second aliquot dispensing device 30 pours out the pretreated specimen A1, which has been sucked from the reaction cell 2a, into the reaction cell 2d. That is, the second aliquot dispensing device 30 can perform suction of the pretreatment solution from the cell 2a (see FIG. 6A) and ejection of the pretreatment solution into the cell 2d (see FIG. 6B) in one position P2. Additionally, during the second period, the stirrer 40 stirs together the specimen C and the pretreatment solution in the reaction cell 2c. Consequently, a pretreated specimen C1 is created in the cell 2c.

Figure 7A:
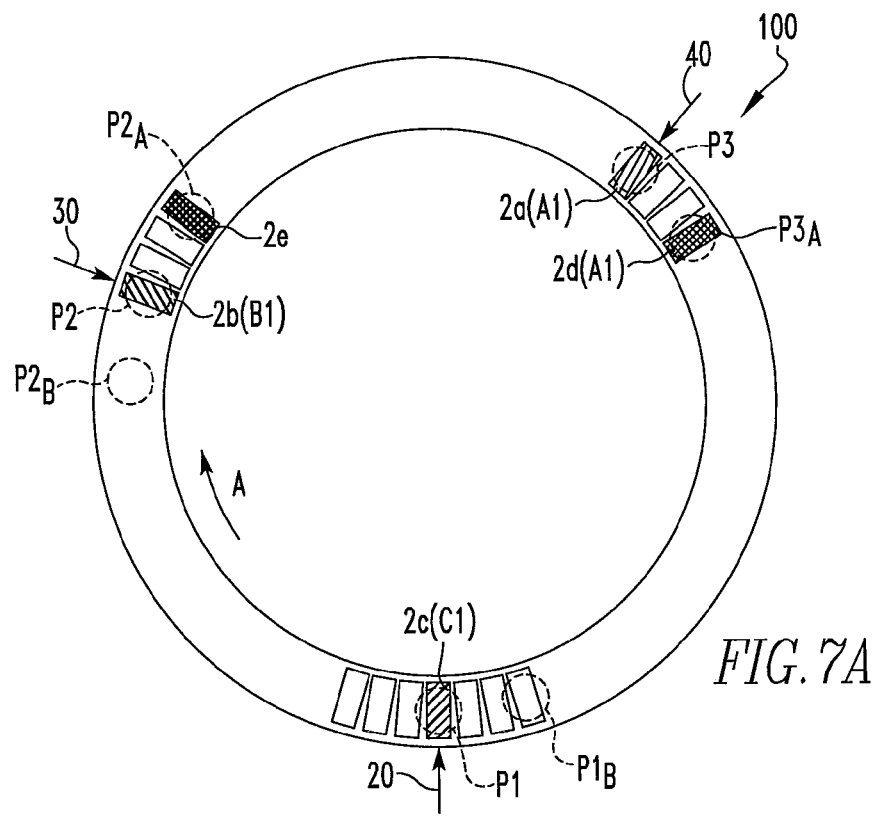
FIGS. 7A and 7B are plan views of the automated analyzer shown in FIG. 1, illustrating the operation.

As shown in FIG. 7A, the controller 10 performs a fifth cycle of the first control operation to cause the turntable 4 to move the reaction cell 2a located in the position P2$_B$ into the third position P3, to move the reaction cell 2d located in the second position P2 into the position P3$_A$, to move the reaction cell 2b located in the position P1$_B$ into the second position P2, to move the reaction cell 2e located in the first position P1 into the fourth position P2$_A$, and to move the reaction cell 2c located in the third position P3 into the first position P1. The cells are halted for the first period of time.

During the first period, the second aliquot dispensing device 30 sucks the pretreated specimen B1 from within the reaction cell 2b.

Figure 7B:
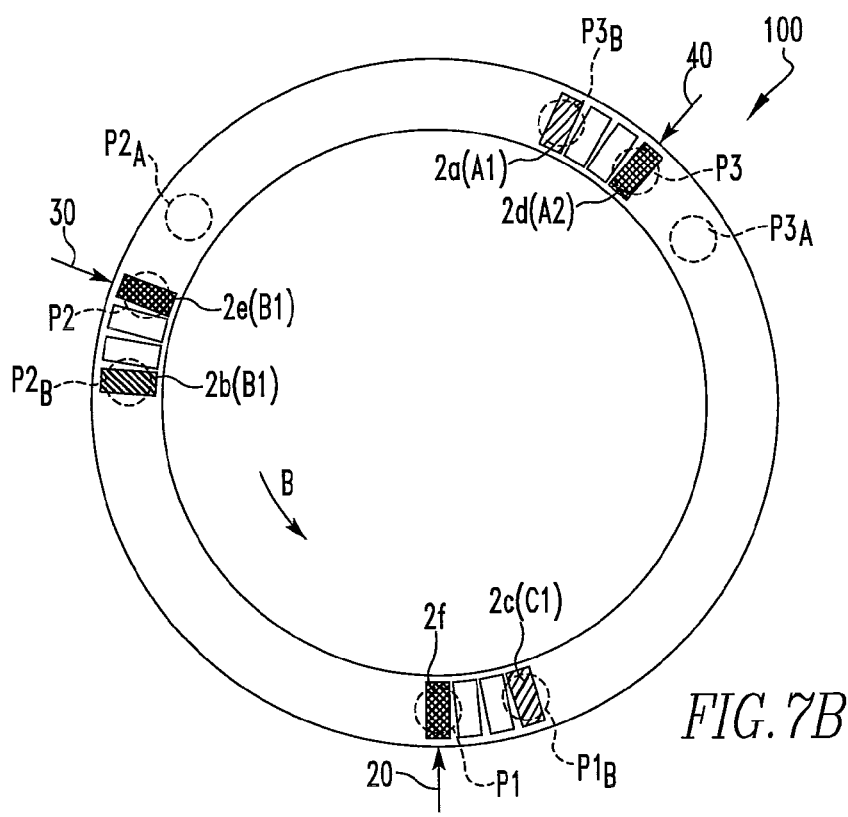

As shown in FIG. 7B, the controller 10 performs a fifth cycle of the second control operation to cause the turntable 4 to move the reaction cell 2a located in the third position P3 into a position P3$_B$ spaced by the second angle in the second direction B from the third position P3, to move the reaction cell 2d located in the position P3$_A$ into the third position P3, to move the reaction cell 2b located in the second position P2 into the position P2$_B$, to move the reaction cell 2e located in the fourth position P2$_A$ into the second position P2, and to move the reaction cell 2c located in the first position P1 into the position P1$_B$. The cells are halted in the second period of time.

During the second period, the first aliquot dispensing device 20 pours out a reagent into a reaction cell 2f halted in the first position P1. For example, the cell 2f is spaced by the second angle in the first direction A from the reaction cell 2c. Furthermore, during the second period, the second aliquot dispensing device 30 pours out the pretreated specimen B1, which has been drawn in from the reaction cell 2b, into the reaction cell 2e. Additionally, during the second period, the stirrer 40 stirs together the pretreated specimen A1 and the reagent in the cell 2d. Consequently, a reacted specimen A2 is created inside the cell 2d by the reaction of the pretreated specimen A1 with the reagent.

Figure 8A:
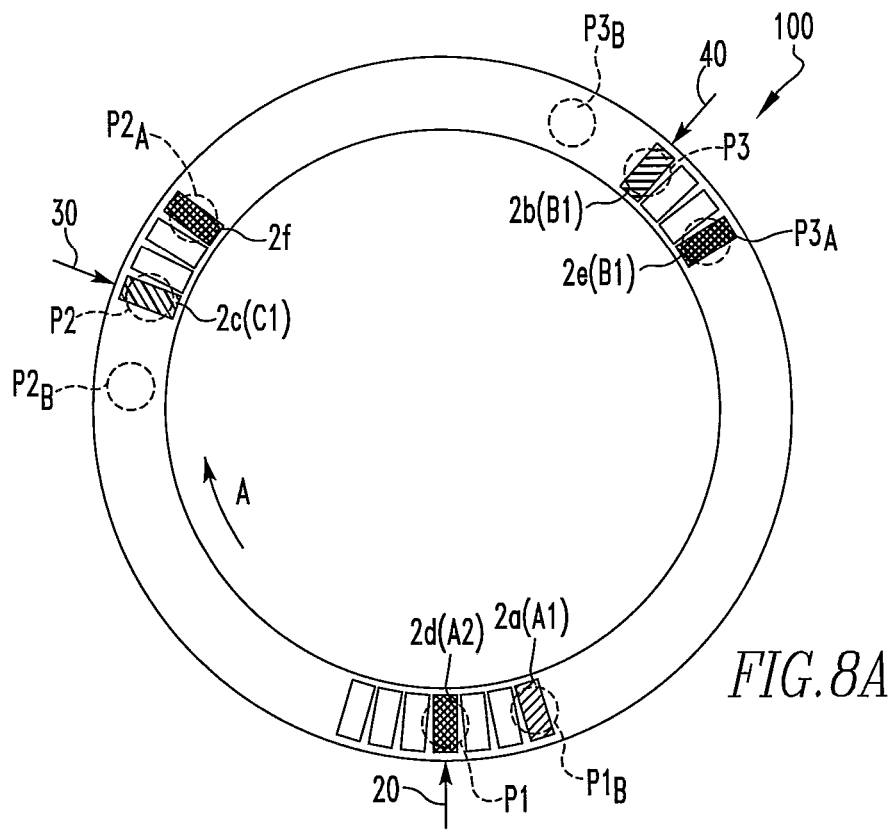
FIGS. 8A and 8B are plan views of the automated analyzer shown in FIG. 1, illustrating the operation.

As shown in FIG. 8A, the controller 10 performs a sixth cycle of the first control operation to cause the turntable 4 to move the reaction cell 2a located in the position P3$_B$ into the position P1$_B$, to move the reaction cell 2d located in the third position P3 into the first position P1, to move the reaction cell 2b located in the position P2$_B$ into the third position P3, to move the reaction cell 2e located in the position P2$_B$ into the position P3$_A$, to move the reaction cell 2c located in the position P1$_B$ into the second position P2, and to move the reaction cell 2f located in the first position P1 into the fourth position P2$_A$. The cells are halted for the first period of time.

During the first period, the second aliquot dispensing device 30 sucks the pretreated specimen C1 from within the reaction cell 2c.

Figure 8B:
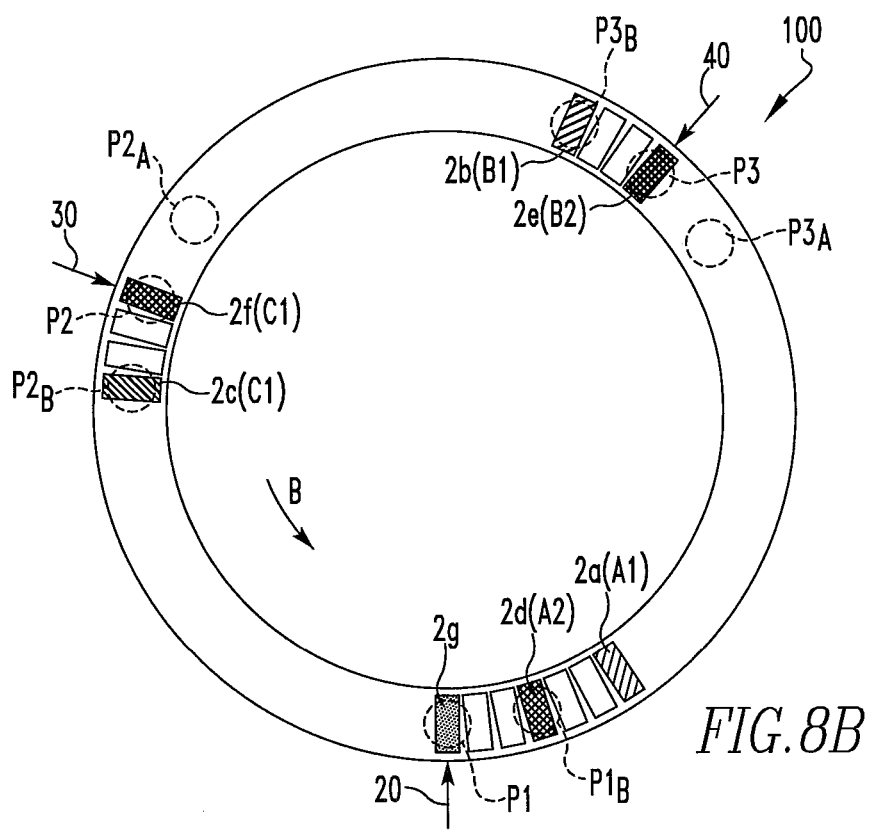

As shown in FIG. 8B, the controller 10 performs a sixth cycle of the second control operation to cause the turntable 4 to move the reaction cell 2d located in the first position P1 into the position P1$_B$, to move the reaction cell 2b located in the third position P3 into the position P3$_B$, to move the reaction cell 2e located in the position P3$_A$ into the third position P3, to move the reaction cell 2c located in the second position P2 into the position P2$_B$, and to move the reaction cell 2f located in the position P2$_A$ into the second position P2. The cells are halted for the second period.

During the second period, the first aliquot dispensing device 20 pours out a pretreatment solution into a reaction cell 2g halted in the first position P1. For example, the cell 2g is spaced by the second angle in the first direction A from the reaction cell 2d. Furthermore, during the second period, the second aliquot dispensing device 30 pours out the pretreated specimen C1, which has been drawn in from the reaction cell 2c, into the reaction cell 2f. In addition, during the second period, the stirrer 40 stirs together the pretreated specimen B1 and reagent inside the reaction cell 2e. In consequence, a reacted specimen B2 is created within the cell 2e by the reaction of the pretreated specimen B1 with the reagent.

Figure 9A:
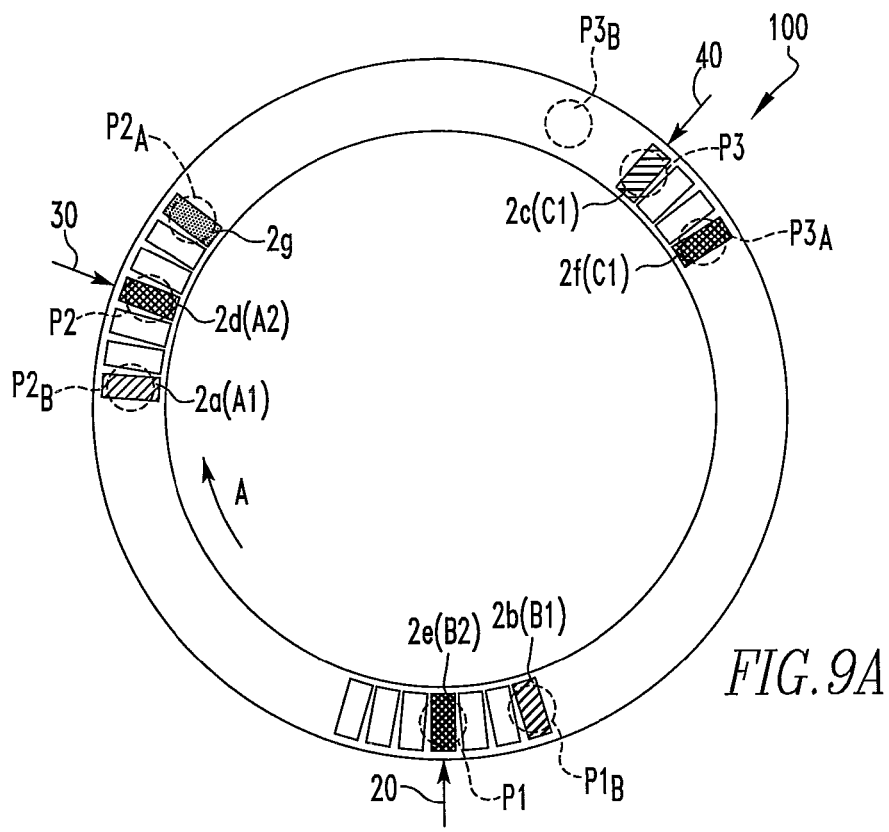
FIGS. 9A and 9B are plan views of the automated analyzer shown in FIG. 1, illustrating the operation.

As shown in FIG. 9A, the controller 10 performs a seventh cycle of the first control operation to cause the turntable 4 to move the reaction cell 2g located in the first position P1 into the position $P2_A$, to move the reaction cell 2e located in the third position P3 into the first position P1, and to move the reaction cell 2f located in the second position P2 into the position $P3_A$.

Figure 9B:
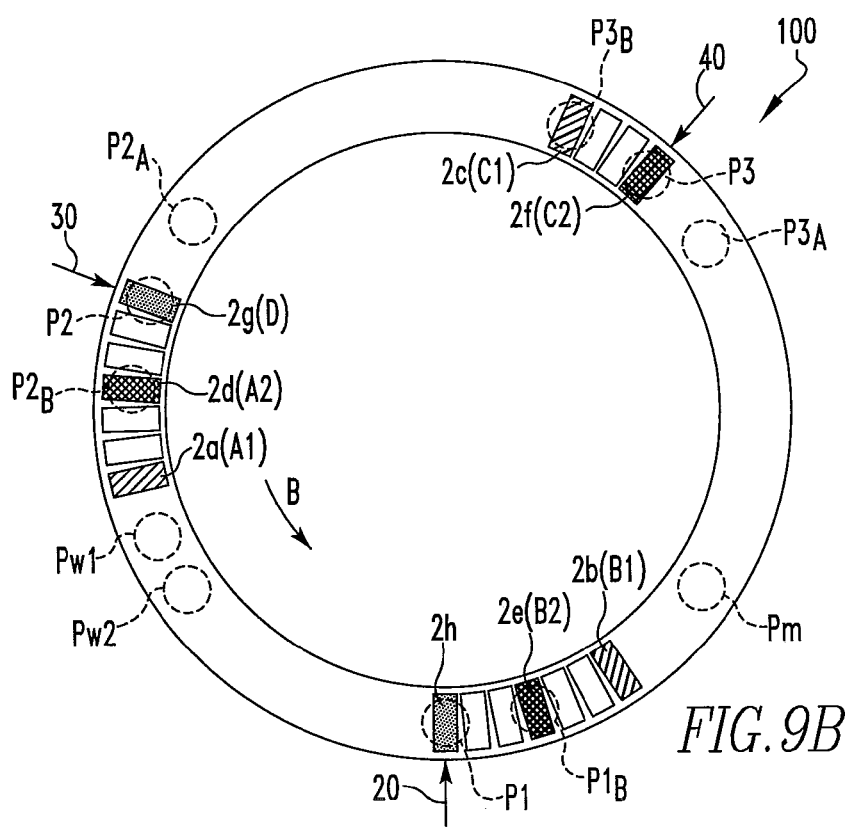

As shown in FIG. 9B, the controller 10 performs a seventh cycle of the second control operation to cause the turntable 4 to move the reaction cell 2g located in the position $P2_A$ into the second position P2, to move the reaction cell 2e located in the first position P1 into the position $P1_B$, and to move the reaction cell 2f located in the position $P3_A$ into the third position P3. The cells are halted for the second period of time.

During the second period, the first aliquot dispensing device 20 pours out a reagent into a reaction cell 2h halted in the first position P1. For example, the cell 2h is spaced by the second angle in the first direction A from the reaction cell 2e. Furthermore, during the second period, the second aliquot dispensing device 30 pours out a specimen D into the reaction cell 2g. In addition, during the second period, the stirrer 40 stirs together the pretreated specimen C1 and reagent in the reaction cell 2f. In consequence, a reacted specimen C2 is created in the reaction cell 2f by the reaction of the pretreated specimen C1 with the reagent.

The measuring instrument 50 (see FIG. 1) measures the reacted specimens A2, B2, and C2 in the reaction cells 2d, 2e, and 2f, respectively, whenever the reaction cells 2e, 2e, and 2f pass across the measurement position Pm.

The cleaning device 60 cleans each reaction cell 2 undergone a measurement when it is halted at the cleaning positions Pw1 and Pw2.

Because of the processing steps described so far, the automated analyzer 100 can analyze the specimens A, B, and C.

Table I is a table illustrating the flow of operation of the first aliquot dispensing device 20. Table II is a table illustrating the flow of operation of the second aliquot dispensing device 30. Table III is a table illustrating the flow of operation of the stirrer 40.

As shown in Tables I, II, and III, the first aliquot dispensing device 20 successively injects aliquots of pretreatment solution from the zeroth cycle to the second cycle. The dispensing device can successively inject aliquots of reagent from the third to fifth cycle. In this way, the automated analyzer 100 can operate the first aliquot dispensing device 20 without interruption.

TABLE I

Flow of operation of the first aliquot dispensing device

| Cycle | Operation |
|---|---|
| 0 | Injection of pretreatment solution (Specimen A) |
| 1 | Injection of pretreatment solution (Specimen B) |
| 2 | Injection of pretreatment solution (Specimen C) |
| 3 | Injection of reagent (pretreated Specimen A1) |
| 4 | Injection of reagent (pretreated Specimen B1) |
| 5 | Injection of reagent (pretreated Specimen C1) |
| 6 | Injection of pretreated solution (Specimen D) |
| 7 | Injection of pretreated solution (Specimen E) |

The second aliquot dispensing device 30 can successively inject aliquots of the specimens A, B, and C from the first to third cycle. The device can successively inject aliquots of the pretreated specimens A1, B1, and C1 from the fourth to sixth cycle. In this way, the automated analyzer 100 can operate the second aliquot dispensing device 30 ceaselessly.

TABLE II

Flow of operation of the second aliquot dispensing device

| Cycle | Operation |
|---|---|
| 0 | No operation |
| 1 | Injection of Specimen A |
| 2 | Injection of Specimen B |
| 3 | Injection of Specimen C |
| 4 | Injection of pretreated Specimen A1 |
| 5 | Injection of pretreated Specimen B1 |
| 6 | Injection of pretreated Specimen C1 |
| 7 | Injection of Specimen D |

The stirrer 40 can successively stir each of the specimens A, B, and C and the pretreatment solution from the second to fourth cycle. The stirrer can successively stir each of the pretreated specimens A1, B1, and C1 and the reagent from the fifth to seventh cycle. In this way, the automated analyzer 100 can operate the stirrer 40 without cessation from the first cycle onward. In this manner, the automated analyzer 100 can operate the devices 20, 30, and 40 efficiently.

TABLE III

Flow of operation of stirrer

| Cycle | Operation |
|---|---|
| 0 | No operation |
| 1 | No operation |
| 2 | Stirring between Specimen A and pretreatment solution |
| 3 | Stirring between Specimen B and pretreatment solution |
| 4 | Stirring between Specimen C and pretreatment solution |
| 5 | Stirring between pretreated Specimen A1 and reagent |
| 6 | Stirring between pretreated Specimen B1 and reagent |
| 7 | Stirring between pretreated Specimen C1 and reagent |

In the description of the above-described processing steps, the three specimens A, B, and C are analyzed. The automated analyzer 100 can analyze more than three specimens by repeating the above-described processing steps.

The automated analyzer 100 has various features. Examples of the features are described below.

The automated analyzer 100 performs the first control operation and the second control operation. In the first control operation, the controller 10 rotates the turntable 4 through the first angle in the first direction A and then halts the turntable. In the second control operation, the controller rotates the turntable 4 through the second angle in the second direction B and then halts it. Thus, while the turntable 4 is making its first rotation, the first reaction cells 2a, 2b, and 2c are halted in the first position P1, second position P2, and third position P3, and the first processing operation can be performed. Then, while the turntable is making its second rotation, the first reaction cells 2a, 2b, and 2c are again halted in the first position P1, second position P2, and third position P3. Also, the corresponding second reaction cells 2d, 2e, and 2f are halted in the first position P1, second position P2, and third position P3, and the second processing operation can be performed. Therefore, the first and second processing operations can be carried out on the same turntable 4. In addition, the first aliquot dispensing device 20, second aliquot dispensing device 30, and stirrer 40 can perform processing efficiently at their respective one positions. Accordingly, the processing capabilities can be improved without increasing the size of the instrument or complicating it. For example, in an automated analyzer using a turntable rotating through a given angle in a given direction per unit time, in order to inject aliquots of the pretreated specimen from the reaction cell in which the pretreated specimen has been created into other reaction cells, suction and delivery steps must be performed at least in two positions on the turntable. Therefore, the aliquot dispensing device for injecting aliquots of the pretreated specimen needs to have, for example, a mechanism for moving across the two positions. The automated analyzer 100 dispenses with such a mechanism. Hence, the processing capabilities can be enhanced without increasing the size of the instrument or complicating it.

The automated analyzer 100 permits the first aliquot dispensing device 20, second aliquot dispensing device 30, and stirrer 40 to be operated efficiently as shown in FIGS. 10-12. Consequently, the processing capabilities can be enhanced.

After injecting aliquots of reagent into the reaction cells 2, the automated analyzer 100 can inject aliquots of a pretreated specimen into the reaction cells 2. That is, the second aliquot dispensing device 30 can inject aliquots of the pretreated specimen into the reaction cells 2 in which the aliquots of reagent have been held. Consequently, when the second aliquot dispensing device 30 injects the pretreated specimen into the reaction cells 2, it is easy to pour out the pretreated specimen because there is the reagent inside the cells 2. Especially, this method is effective where small amounts of pretreated specimen are poured out by the second aliquot dispensing device 30.

It is to be understood that the present invention is not restricted to the foregoing embodiment and its modifications and that various changes and modification can be made thereto without departing from the gist and scope of the present invention.

For example, in the description of the above embodiment, the automated analyzer 100 performs the first and second processing operations for all of the specimens A, B, and C. The analyzer 100 may perform only the second processing operation, for example, on some specimens without performing the first processing operation. That is, the analyzer 100 may treat specimens subjected to the first processing operation as well as specimens not subjected to the first processing operation. Even in this case, the devices 20, 30, and 40 can be operated efficiently by making the controller 10 perform the first and second control operations in the same way as in the foregoing embodiment.

Furthermore, in the description of the above embodiment, the second aliquot dispensing device 30 injects aliquots of specimen after the first aliquot dispensing device 20 injects aliquots of pretreatment solution. After the first aliquot dispensing device 20 injects aliquots of reagent, the second aliquot dispensing device 30 injects aliquots of pretreatment solution. Instead, the first aliquot dispensing device 20 may inject aliquots of pretreatment solution after the second aliquot dispensing device 30 injects aliquots of specimen, and the first aliquot dispensing device 20 may inject aliquots of reagent after the second aliquot dispensing device 30 injects aliquots of pretreated specimen. In this case, the first aliquot dispensing device 20 and the second aliquot dispensing device 30 as shown in FIG. 1 may be positionally interchanged.

In addition, in the above embodiment, the first aliquot dispensing device 20, cleaning device 60, second aliquot dispensing device 30, controller 10, stirrer 40, and measuring instrument 50 are arranged in this order in a clockwise direction around the periphery of the turntable 4 as shown in FIG. 1. No restrictions are placed on the positions of the devices 10-60.

Further, in the description of the above embodiment, the automated analyzer 100 has the single first aliquot dispensing device 20 for injecting aliquots of pretreated solution and reagent as shown in FIG. 1. The analyzer may have plural first aliquot dispensing devices, in which case it is easy to inject aliquots of plural pretreatment solutions and plural reagents into the reaction cells 2. The first aliquot dispensing devices may perform processing, for example, at plural positions.

Additionally, in the description of the above embodiment, the automated analyzer 100 has the single stirrer 40. Instead, the analyzer may have plural stirrers, which may perform processing, for example, at plural positions. In this case, processing is performed at three or more positions P1, ..., Pn (n is an integer equal to or greater than 3). In this situation, the angle made between the position P1 at which the first processing is performed and the position Pn at which the final processing is effected is equal to the first angle. The angle made between the successive positions is equal to the difference between the first and second angles. The second reaction cells 2 in which the second processing operation is performed are spaced by the second angle in the first direction A from the first reaction cells 2 in which the first processing operation is performed. Consequently, it is possible to obtain the same advantageous effects as yielded by the above embodiment.

The present invention embraces configurations substantially identical (e.g., in function, method, and results or in purpose and advantageous effects) with the configurations described in the preferred embodiment of the invention. Furthermore, the invention embraces the configurations described in the embodiment including portions which have replaced non-essential portions. In addition, the invention embraces configurations which produce the same advantageous effects as those produced by the configurations described in the preferred embodiment or which can achieve the same objects as the objects of the configurations described in the preferred embodiment. Further, the invention embraces configurations which are the same as the configurations described in the preferred embodiment and to which well-known techniques have been added.

Having thus described my invention with the detail and particularity required by the Patent Laws, what is desired protected by Letters Patent is set forth in the following claims.

The invention claimed is:

1. An automated analyzer for performing a first processing operation to create a pretreated specimen by pretreating a specimen with a pretreatment solution in a first set of reaction cells and a second processing operation to create a reacted specimen by reacting the pretreated specimen with a reagent in a second set of reaction cells, said automated analyzer comprising:

a turntable on which the first and second reaction cells are arranged annularly;

controller for controlling rotation of the turntable;

first aliquot dispenser for selectively pouring out either the pretreatment solution or the reagent into reaction cells positioned at a first position around the turntable;

second aliquot dispenser for selectively performing dispensing of aliquots of the specimen into the first reaction cells or injection of aliquots of the pretreated specimen into the second reaction cells at a second position around the turntable;

a stirrer for selectively performing stirring of the pretreatment solution and the specimen in the first reaction cells and stirring of the pretreated specimen and the reagent in the second reaction cells at a third position around the turntable; and measuring means instrument for measuring the reacted specimen;

wherein said controller repeatedly performs a first control operation for rotating the turntable through a first angle in a first direction and then bringing the turntable to a halt and a second control operation for rotating the turntable through a second angle in a second direction opposite to the first direction and then bringing the turntable to a halt;

wherein said second reaction cells are spaced by the second angle in the first direction from the first reaction cells;

wherein the turntable is so rotated that the first and second reaction cells are halted at least in the first, second, and third positions by repetitive execution of the first control operation and the second control operation; and wherein said second aliquot dispensing means sucks the pretreated specimen from the first reaction cell when the first reaction cell containing the pretreated specimen is halted in the second position and pours out the sucked pretreated specimen into the second reaction cell when the second reaction cell is halted in the second position.

2. The automated analyzer of claim 1, wherein an angle made between the first position and the second position and an angle made between the second position and the third position are equal to a difference between the first angle and the second angle, and wherein an angle made between the third position and the first position is equal to the first angle.

3. The automated analyzer of any one of claims 1 and 2, wherein owing to the first control operation and the second control operation, said turntable moves the first reaction cell located in the first position into a fourth position spaced by the second angle in the first direction from the second position, halts the cell, then moves the cell from the fourth position into the second position, and halts the cell, moves the first reaction cell located in the second position into a fifth position spaced by the second angle in the first direction from the second position, halts the cell, then moves the cell from the fifth position into the third position, and then halts the cell, moves the first reaction cell located in the third position into the first position, halts the cell, then moves the cell into a sixth position spaced by the second angle in the second direction from the first position, and halts the cell, and moves the first reaction cell located in the sixth position into the second position, halts the cell, then moves the cell into a seventh position spaced by the second angle in the second direction from the second position, and halts the cell.

4. The automated analyzer of any one of claims 1 to 2, wherein said second angle is smaller than said first angle.

5. The automated analyzer of any one of claims 1 to 2, wherein said second aliquot dispensing device injects aliquots of said pretreated specimen into the second reaction cells in which aliquots of the reagent have been injected.

6. The automated analyzer of any one of claims 1 to 2, further comprising a spectrometer which directs light at a specimen reacted with the reagent existing in the reaction cell passing across an arbitrary position on the turntable and electrically detects the amount of light transmitted through the specimen.

7. The automated analyzer of any one of claims 1 to 2, wherein a first cleaning position is set at an arbitrary position on the turntable, and wherein there is further provided a waste liquid pump for drawing in unwanted fluids from the reaction cell halted in the first cleaning position and discharging the unwanted fluids into a waste tank, the unwanted fluids including the already measured, reacted specimen and the pretreated specimen no longer required.

8. The automated analyzer of claim 7, wherein a second cleaning position is set at another arbitrary position on the turntable, and wherein there is further provided a cleaning liquid pump for supplying a cleaning liquid into the reaction cell, from which the unwanted fluids have been discharged, at the second cleaning position to clean the interior of the reaction cell with the cleaning liquid.

9. The automated analyzer of claim 8, wherein said cleaning liquid pump cleans the reaction cell with the cleaning liquid and then discharges the cleaning liquid into the waste liquid tank.

\* \* \* \* \*